United States Patent [19]
Mori

[11] Patent Number: 4,699,086
[45] Date of Patent: Oct. 13, 1987

[54] UNDERWATER FISH FEEDING PLANT

[76] Inventor: Kei Mori, 3-16-3-501, Kaminoge, Setagaya-ku, Tokyo, Japan

[21] Appl. No.: 793,024

[22] Filed: Oct. 30, 1985

[30] Foreign Application Priority Data

Nov. 9, 1984 [JP] Japan .................................. 59-237358

[51] Int. Cl.$^4$ ........................................... A01K 61/00
[52] U.S. Cl. .................................... 119/3; 47/1.4
[58] Field of Search ............... 119/3; 47/1.4; 126/425, 126/440; 405/218, 221, 70, 220, 195, 219, 211, 218, 221, 224, 21, 23, 24, 25–30, 32, 33, 34, 35, 63, 64, 71, 201–205, 210.60; 114/264, 265, 266, 256, 314, 326

[56] References Cited

U.S. PATENT DOCUMENTS

| | | | |
|---|---|---|---|
| 2,709,984 | 6/1955 | Marks | 119/3 |
| 3,094,847 | 6/1963 | Pogonowski | 405/204 |
| 3,785,313 | 1/1974 | Rosenberg | 114/266 |
| 3,841,266 | 10/1974 | Hoshino | 119/2 |
| 4,086,161 | 4/1978 | Burton | 47/1.4 X |
| 4,205,625 | 6/1980 | Muller-Feuga | 119/2 |
| 4,324,068 | 4/1982 | Anthony | 47/1.4 |
| 4,335,680 | 6/1982 | Kipping | 119/3 |
| 4,340,812 | 7/1982 | Mori | 126/425 |
| 4,365,576 | 12/1982 | Cook | 405/205 |
| 4,459,643 | 7/1984 | Mori | 362/32 |
| 4,501,084 | 2/1985 | Mori | 43/17.5 |
| 4,612,726 | 9/1986 | Mori | 47/17 X |

FOREIGN PATENT DOCUMENTS

| | | | |
|---|---|---|---|
| 0080414 | 6/1983 | European Pat. Off. | 119/3 |
| EP85926 | 8/1983 | European Pat. Off. | 47/1.4 |
| 1299164 | 7/1969 | Fed. Rep. of Germany | 47/1.4 |
| 105444 | 6/1985 | Japan | 47/1.4 |

Primary Examiner—Richard T. Stouffer
Assistant Examiner—Danton DeMille
Attorney, Agent, or Firm—Jordan and Hamburg

[57] ABSTRACT

A fish feeding plant utilizing a solar ray collecting device and a algae cultivating device installed in the sea, the lake, or the pond, etc. The plant comprises a structure made of cylinders and constructed by vertically setting up cylinders in water and connecting the respective cylinders with each other by use of horizontal cylinders, a solar ray collecting device installed on the water surface above the structure, and a culture device for cultivating algae or the like installed in water. Solar rays collected by the solar ray collecting device being transmitted to the culture device for cultivating the algae or the like through an optical conductor cable and employed as a photo-synthesis light source for the algae or the like. The culture device cultivating the algae or the like by utilizing carbon dioxide $CO_2$, phosphorus, nitrogen, nutritious salt, etc. contained in water, and algae or the like created by cultivation and carbon dioxide $CO_2$ being discharged into water.

7 Claims, 4 Drawing Figures

UNDERWATER FISH FEEDING PLANT

BACKGROUND OF THE INVENTION

The present invention relates to a fish feeding plant, in particular, a fish feeding plant effectively utilizing a solar ray collecting device and a algae cultivating device.

The present applicant has previously proposed various ways to focus solar rays or artificial light rays by the use of lenses or the like, to guide the same into an optical conductor cable, and thereby to transmit them onto an optional desired place through the optical conductor cable. The solar rays or the artificial light rays transmitted and emitted in such a way are employed for photo-synthesis and for use in illuminating or for other purposes, as for example to promote the cultivation of plants or to cultivate algae or the like.

Furthermore, the present applicant has already proposed various culture devices for cultivating algae or the like, as for instance, chlorella. Basically, in order to cultivate chlorella, light rays and carbon dioxide $CO_2$ are needed for performing photo-synthesis. By supplying light rays and carbon dioxide $CO_2$ to a chlorella cultivating tub, the chlorella is cultivated, and the oxygen $O_2$ is created at the same time.

As mentioned above, the solar rays or the artificial light rays are focused by use of lenses or the like and guided into an optical conductor and further guided into a chlorella cultivating tub through an optical conductor. The light rays are radiated from the optical conductor in the chlorella cultivating tub and supplied to a desired place. On the other hand, for supplying carbonic acid gas thereto, commercially prepared carbon dioxide $CO_2$ is purchased and supplied to the chlorella.

The chlorella produced in such a manner as mentioned above is employed as a food for cultivating fish or the like. This method has never been tried until now i.e. that the chlorella cultivating device is installed directly in water and utilized for feeding fish.

SUMMARY OF THE INVENTION

It is an object of the present invention to provide a fish feeding device.

it is another object of the present invention to provide a fish feeding plant utilizing a solar ray collecting device and a algae or chlorella cultivating device.

It is another object of the present invention to effectively feed the fish by use of a chlorella cultivating device installed directly in water.

It is another object of the present invention to provide a fish feeding plant possible to construct a large-scaled and effective fish feeding plant in the sea, the lake, or the pond, etc.

It is another object of the present invention to effectively concentrate and feed the fish by use of a chlorella cultivating device installed directly in water and further to improve water quality.

The above-mentioned features and other advantages of the present invention will be apparent from the following detailed description which goes with the accompanying drawings.

DESCRIPTION OF THE PREFERRED EMBODIMENT

Figure 1:
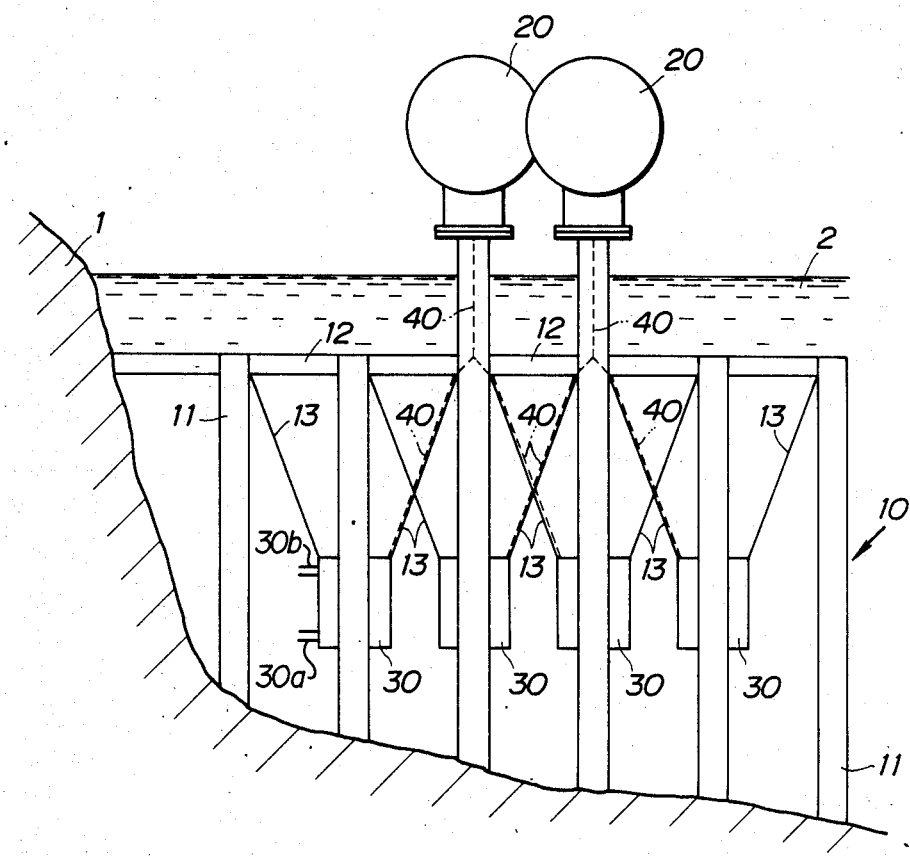
FIG. 1 is a side elevational construction view for explaining an embodiment of a fish feeding plant according to the present invention.
Figure 2:
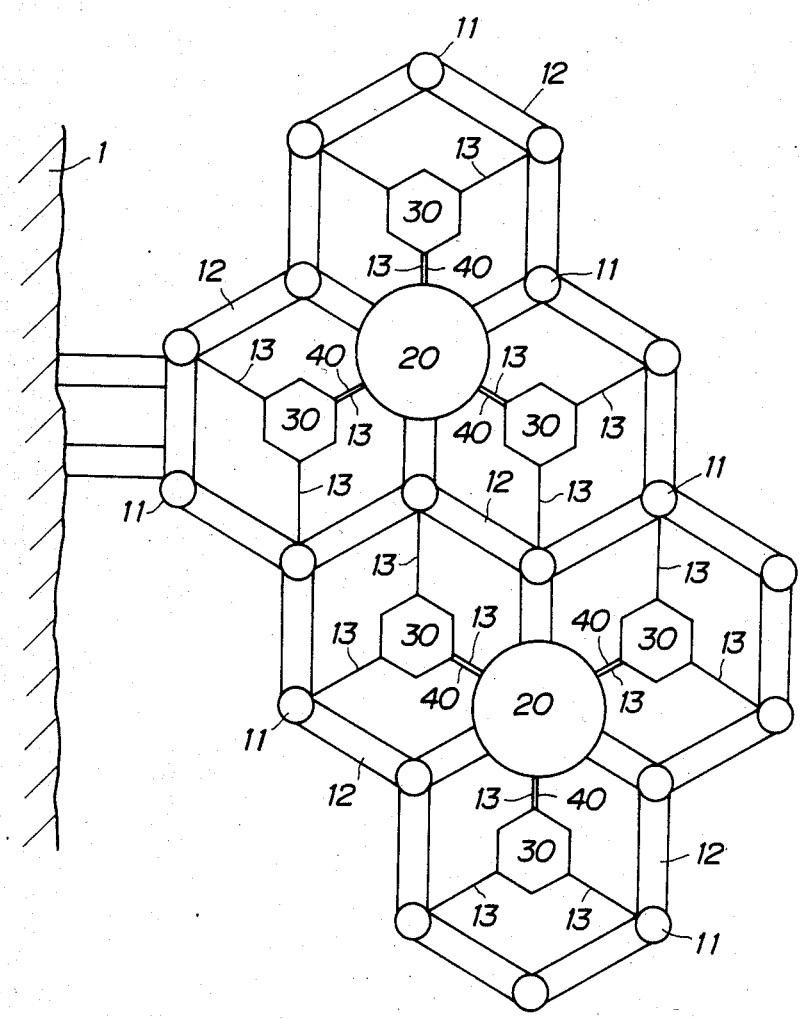
FIG. 2 is a plan view thereof.

FIG. 1 is a side elevational construction view for explaining an embodiment of a fish feeding plant according to the present invention and FIG. 2 is a plan view of the same. In FIGS. 1 and 2, 1 is the earth's crust, 2 a space in water, 10 a a structure constructed in water, 20 a solar ray collecting device, and 30 a culture device for cultivating algae or the like such as chlorella. The afore-mentioned structure consists of a large number of cylinders 11 set up vertically on the earth's crust 1, a large number of horizontal cylinders 12 connecting the respective cylinders 11 with each other, and suspended members 13 for suspending the chlorella cultivating device 30.

However, all of the afore-mentioned cylinders are set up vertically at the respective vertexes of the hexagon as shown in FIG. 2 and the chlorella cultivating device is installed in the hexagon formed by the cylinders 11. Consequently, all of the distances between the respective chlorella cultivating devices turn out to be equal and therefore it follows that fish feeding territories of uniform quality can be created. Also an additional construction can be easily added.

Each hollow cylinder has an inner space that a person can easily pass through so that the chlorella cultivating device and the structure can be easily observed through the hollow cylinder. Furthermore, an optical conductor cable 40 for transmitting light rays collected by the solar ray collecting device is installed through the hollow cylinder or along the side of the suspended members 13.

Only the hollow cylinders on which the solar ray collecting device is equipped project above the water's surface while the other hollow cylinders are set up below the water's surface so as to allow a ship to cruise above the structure 10. In such a manner, the chlorella cultivating device and the structure can be observed from a ship cruising above them. The height of the cylinders' portion projecting above the water surface and the depth of the same which is below the water's surface are determined in consideration of the ebb and flow of the tide. Namely, the dimensions of the cylinders are designed in such a manner that the solar ray collecting device 20 does not sink under the water's surface at the time of floods or typhoons and the structure 10 does not appear above the water's surface at ebb-tide. Furthermore, if the dimensions thereof are designed as mentioned above, almost an entire portion of the structure 10 sinks under the water's surface so that the structure is always protected safely without being effected by tidal waves.

Furthermore, if the plant is constructed in such a manner that the solar ray collecting device is removably connected with the optical conductor cable for transmitting the solar rays collected by the solar ray collecting device, the solar ray collecting device can be disconnected from the optical conductor cable, removed therefrom, carried by the ship, and stored during a typhoon, etc.

An embodiment of the fish feeding plant in which the chlorella is cultivated by use of the solar rays collected by the solar ray collecting device 20 has been described heretofore. However, if the solar battery, the storage battery charged by the solar battery and/or the generator and the artificial light source, etc. are equipped in the plant, and the light rays emitted from the artificial light source are supplied to the chlorella cultivating device through the optical conductor cable, the chlorella can be cultivated even when the solar rays are very faint in brightness or cannot be collected at all during the night.

When the outer circumferential surface of the chlorella cultivating device 30 is constructed with a transparent substance, the light rays employed for cultivating the chlorella will leak from the chlorella cultivating device. Therefore, it not only will gather fish seeking the light rays which leak therefrom, but also algae sticks to the outer surface of the chlorella cultivating device, seeking the same. As a result, the device has a green color and fish are attracted by light rays of a green color. Furthermore, since algae is a bait for the animal plankton, the latter eats the former and grows. The fish eat the mature plankton. In such a manner, a food chain is formed and fish are cultivated. The outer circumferential surface of the chlorella cultivating tub will also be cleaned in this manner. Furthermore, when a part of the solar rays or the artificial light rays, focused in such a manner as mentioned before, is radiated from the upper portion of the chlorella cultivating device, a large number of fish will come together around the device. As a result, fish feeding will be performed much more effectively.

And is previously proposed by the present applicant in Japanese Patent Application No. 165123/1984, the respective chlorella cultivating devices comprise an inlet opening for taking in external water, for instance, sea-water in the case of constructing the plant according to the present invention in the sea, and an outlet opening for discharging the cultivated chlorella and/or the oxygen $O_2$ created by cultivating the chlorella. The carbon dioxide $CO_2$, phosphorus, nitrogen, nutritious salt, etc. contained in water are taken into the chlorella cultivating device 30 through the inlet openings 30a in order to cultivate the chlorella. Then the cultivated chlorella and/or the oxygen $O_2$, created by cultivating the chlorella, are discharged back into the sea through the outlet opening 30b.

Consequently, it follows that the substance needed for cultivating chlorella is taken in from the sea and oxgyen $O_2$ and the food needed for feeding the fish are produced in the chlorella cultivating device 30 and discharged back into the sea. Therefore, it may be possible to perform fish-feeding at a lower cost and more effectively and it may be possible to improve water's quality.

Figure 3:
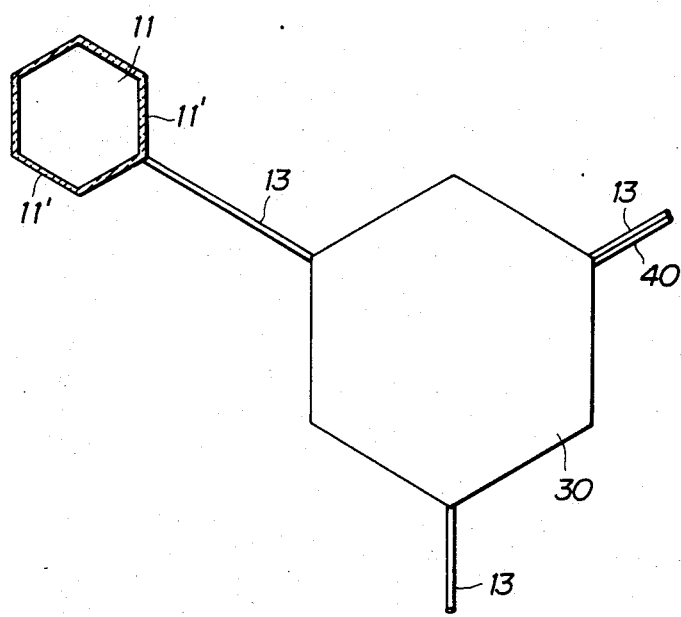
FIG. 3 is a cross-sectional construction view showing an embodiment of the cylinder installed vertically.

FIG. 3 is a cross-sectional construction view showing an embodiment of the above-mentioned cylinder 11 set up vertically. As shown in FIG. 3, the cylinder 11 is constructed in the shape of a hexagon and its side wall 11' is constructed with a transparent substance so that the conditions in water of the chlorella cultivating device can be observed through the transparent wall member 11'. Needless to say, a ladder is installed in the cylinder in a vertical position.

Figure 4:
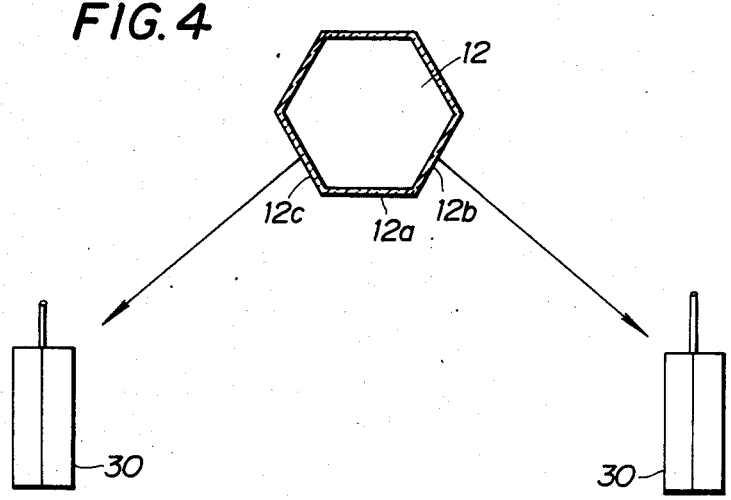
FIG. 4 is a cross-sectional construction view showing an embodiment of the cylinder installed horizontally.

FIG. 4 is a cross-sectional construction view showing an embodiment of the above-mentioned cylinder 12 installed horizontally. As shown in FIG. 4, the horizontal cylinder 12 is constructed in the shape of a hexagon and its bottom surface 12a is horizontal. If both of the inclined surfaces 12b and 12c neighboring the bottom surface are constructed with a transparent substance, a person can walk easily in the hollow cylinder 12 and observe the conditions in water of the chlorella cultivating device. The vertical cylinders and the horizontal cylinders can be constructed entirely with transparent members, otherwise only a necessary part of them can be constructed with transparent members.

As is apparent from the foregoing description, according to the present invention, it will be possible to construct a large-scaled and effective fish feeding plant in the sea, a lake, or a pond, etc. and at the same time, it will be possible to improve the water quality.

I claim:

1. A fish feeding plant comprising a plurality of elongated first hollow bodies each having an elongated axis, each of said first hollow bodies being vertically disposed within a body of water, a plurality of elongated second hollow bodies each having an elongated axis, each of said second hollow bodies being horizontally disposed and being connected to said first hollow bodies to form an interconnected structure disposed within a body of water, said second hollow bodies being formed in the configuration of a plurality of interconnected hexagons with at least one second hollow body of each hexagon being common with at least one second hollow body of another hexagon, each of said hexagons having angled corners, said first hollow bodies being located at each of said angled corners to thereby support said structure within said body of water, a culture device for cultivating algae, suspension means for suspending said culture device from said structure such that said culture device is disposed within said body of water, solar ray collecting means mounted on said structure for collecting solar rays, said solar ray collecting means being disposed above said body of water, optical conductor cable means on said structure for transmitting the collected solar rays from said solar ray collecting means to said culture device for cultivating algae, said culture device thereby cultivating said algae utilizing said transmitted solar rays as a photo-synthesis light source, said culture device having inlet means for taking in carbon dioxide, phosphorus, nitrogen, and salt contained in said body of water, said culture device having outlet means for discharging said algae cultivated by said culture device into said body of water for the feeding of fish.

2. A fish feeding plant according to claim 1 wherein at least portions of at least some of said first and second hollow bodies are transparent, said hollow bodies accommodating persons therein such that said persons in said hollow bodies can view the structure and the cultivating device through said transparent portions.

3. A fish feeding plant according to claim 1 wherein at least some of said hollow bodies have six sides with a hexagonal cross-sectional configuration, at least one of said sides being transparent.

4. A fish feeding plant according to claim 1 wherein each of said hexagonal configurations of second hollow bodies defines a centrally disposed area which is substantially in the center of each of said hexagonals, each of said centrally disposed areas having one of said culture devices disposed thereat.

5. A fish feeding plant according to claim 1 wherein said structure has vertically disposed column means extending above the structure and above the level of said body of water, said solar ray collecting means being disposed on said column means above said body of water.

6. A fish feeding plant according to claim 1 wherein said optical conductor cable means radiates light into the surrounding body of water.

7. A fish feeding plant according to claim 1 wherein said culture device comprises an outer wall of transparent material through which light is radiated to the surrounding body of water.

* * * * *